United States Patent [19]

Tai et al.

[11] Patent Number: 5,425,946
[45] Date of Patent: Jun. 20, 1995

[54] VACCINES AGAINST GROUP C NEISSERIA MENINGITIDIS

[75] Inventors: Joseph Y. Tai, Fort Washington, Pa.; Lucjan J. J. Hronowski, Laurel; Sharon Mates, Chevy Chase, both of Md.

[73] Assignee: North American Vaccine, Inc., Beltsville, Md.

[21] Appl. No.: 938,367

[22] Filed: Aug. 31, 1992

[51] Int. Cl.⁶ ............ A61K 39/095; C07K 1/10
[52] U.S. Cl. ............ 424/197.11; 530/403; 530/807
[58] Field of Search ......... 424/92, 197.11, 194.1; 514/2, 8; 530/403, 405, 406, 411, 807; 536/18.5

[56] References Cited

PUBLICATIONS

Frasch, C. E. 1990, Adv. Biotechnol. Processes vol. 13 pp. 123–145.
Costantino, P. et al. 1992, vaccine vol. 10 pp. 691–698.
Dick, W. E. et al. 1989, contrib. Microbiol. Immunol. vol. 10 pp. 48–114.
Beuvery, E. C. et al. 1986 Develop. Biol. Standard, vol. 65, pp. 197–204.
Griffiss, J. M. et al. 1991, Trans. Royal Soc. Tropical Medicine Hygiene, vol. 85, supl, pp. 32–36.
Zollinger, W. D. et al. 1991 Trans. R. Soc. Trop. med. Hyg. vol. 85 Supl pp. 37–43.
Bhattacharjee, A. K. et al. 1975, J. Biol. Chem. vol. 5 pp. 1926–1932.
Jennings, H. J. et al. 1981 J. Immunol. vol. 127, pp. 1011–1018.
Frasch, C. E. 1989, Clin. Microbiol. Rev. vol. 2, pp. 5134–5138.

Primary Examiner—Mary E. Mosher

[57] ABSTRACT

An immunogenic conjugate comprising a modified group C meningococcal polysaccharide (GCMP) coupled to a carrier molecule. The GCMP is modified by O-deacetylation to a varying extent. This modified GCMP conjugate stimulates a strong immunogenic response. The antiserum, produced by immunization with this conjugate, is cross-reactive with the native polysaccharide. In addition, these antisera elicit a class of antibodies that have patent bactericidal activity.

9 Claims, No Drawings

VACCINES AGAINST GROUP C *NEISSERIA MENINGITIDIS*

FIELD OF THE INVENTION

The present invention relates to the preparation of vaccines useful against group C *Neisseria meningitidis* wherein these vaccines comprise conjugates of modified group C capsular polysaccharides.

BACKGROUND OF THE INVENTION

Group C *Neisseria meningitidis* is the cause of a large percentage of bacterial meningitidis worldwide. Current measures to prevent this disease consist of vaccines composed of purified group C capsular polysaccharide. These vaccines are effective in adults but are poorly immunogenic in children. The poor results in infants is highly undesirable since this section of the population has the highest incidence of these infections.

The group C meningococcal polysaccharide (GCMP) is a weak immunogen and, hence, there have been efforts to enhance the immunogenicity of these polysaccharides to expand their usefulness as vaccines. One possible method of achieving this goal, which has shown some promise is by conjugation of these polysaccharides to a carrier, such as a protein.

Various investigators have isolated and purified intact capsular polysaccharides and have covalently coupled them to carrier proteins. These conjugates are more immunogenic than the polysaccharide alone. Many examples can be found in the literature which illustrate the success of these conjugate antigens. One such example, U.S. Pat. No. 4,673,574 describes the use of bacterial capsular polysaccharides conjugated to carrier proteins to form immunogenic compounds. Another example, U.S. Pat. No. 4,356,170 describes the immunogenicity of conjugates consisting of a specific polysaccharide, group A meningococcal polysaccharide (GAMP) coupled to a carrier protein. These conjugates provide an improved method for delivering effective levels of antigen to a host. The disclosures of both of these patents is incorporated in toto herein by reference thereto.

Another method for increasing immunogenicity has shown promise with the group B meningococcal polysaccharide (GBMP) antigens, as seen in U.S. Pat. No. 4,727,136. This method entails the replacement of N-acetyl groups of the sialyl moiety of the polysaccharide with N-propionyl groups followed by conjugation of the modified polysaccharide to a carrier protein. These conjugates are good immunogens and effectively cross-react with the native GBMP. This finding demonstrates that the addition of substituents onto the polysaccharide antigen can create additional immunogenic sites or epitopes for recognition by antibodies.

Vaccines which are currently prepared from O-acetyl-positive group C N. meningitidis are known to be poorly immunogenic. There have been reports that vaccine derived from an O-acetyl-negative variant is immunogenic. See Glode et al. The Journal of Infectious Disease Vol. 139, No. 1, January, 1979 pp. 52–59; Steinkoff et al, Infection and Immunity, October, 1981 pp. 144–146; and Arakere et al, Infection and Immunity, December, 1991, pp. 4349–4356.

Most group C N. meningitidis strains produce an O-acetyl positive (OAc+) polysaccharide in which the O-acetyl groups are distributed exclusively between C-7 and C-8 of its sialic acid residues. Amongst the known OAc-negtive (OAc−) strains is N. meningitidis group C MC 19 bacteria.

It is an object of the present invention to provide a highly immunogenic vaccine comprising a modified group C meningitidis polysaccharide conjugated to a carrier and also to provide a highly immunogenic vaccine containing the conjugate of a carrier and a modified polysaccharide derived from a OAc negtive variant.

SUMMARY OF THE INVENTION

The present invention relates to the chemical modification by O-deacetylation of the *Neisseria meningitidis* group C polysaccharide (GCMP) derived from OAc+ strains and the conjugation of the deacetylated polysaccharide to a carrier to provide an enhanced immunogenic material.

The invention further relates to a method of fragmenting the deacetylated polysaccharide from OAc+ strains and also fragmenting polysaccharide from OAc− strains in order to decrease the effective size of these polysaccharides.

The invention also relates to a method of creating a residue within the deacetylated polysaccharide from OAc+ strains which provides a reactive site for coupling either directly to a carrier material or to a carrier material via a linking molecule.

In addition, this invention relates to an immunogenic conjugate produced by coupling an O-deacetylated meningococcal C polysaccharide or a polysaccharide from an OAc− strain to a carrier material, wherein the polysaccharide and carrier are covalently coupled.

In the present invention a method is disclosed of preparing immunogenic conjugates comprising covalently coupling a carrier material and a O-deacetylated group C polysaccharide of *Neisseria meningitidis* or a polysaccharide from an OAc− strain or fragments of these polysaccharides.

This invention further relates to the use of the conjugate of the O-deacetylated group C polysaccharide or an OAc− polysacchardie as a potent bactericidal vaccine in mammals susceptible to bacterial meningitidis.

DETAILED DESCRIPTION OF THE INVENTION

In order to enhance the immunogenicity of the group C meningococcal polysaccharide (GCMP), a modified GCMP is generated and covalently coupled to a carrier molecule. Additionally, polysaccharide from an OAc− strain either as isolated or in modified form is covalently coupled to a carrier molecule. The polysaccharide conjugate can be formed from a variety of chemical, physical or enzymatic coupling reactions. The coupling technique used is dependent upon the linking agents which might be employed and the reactive groups on the carrier material or molecule. A variety of coupling procedures are known to the skilled artisan and could be readily employed.

The carrier material or molecule is defined herein as any material or molecule having groups capable of being coupled to polysaccharide moieties. Polymeric carrier can be a natural or a synthetic material, and may be water soluble or water insoluble. Carrier materials or molecules are most commonly proteinaceous in nature. In the case of a protein carrier, the protein can be any physiologically tolerated protein having a reactive group available for coupling. Any type of carrier may be used, which contains a primary or a secondary amino group. The reactive free amino groups can conveniently be coupled to polysaccharide via moieties, such as hydroxyls, aldehydes, carboxylic acids and the like. Suitable proteins include natural peptides and proteins, such as bovine serum albumin, bacterial toxoids derived from bacterial toxins by their synthetic modification, e.g. diphtheria toxoid, tetanus toxoid, Pertussis toxin or Pertussis toxoid, Pseudomonas aeruginosa recombinant exoprotein A and Clostridium perfringens exotoxins. Other proteins derived from bacteria may also be employed. The bacterial source may be, for example, Hemophilus influenza, meningococci, pneumococci $\beta$-hemolytic streptococci and E. Coli. Other proteins containing lysine residues, such as a synthetic polylysine may also be useful. Other protein carriers as well as other non-proteinaceous carrier molecules are readily known to those skilled in the art and could be used as a carrier molecule in the present invention. Examples of water insoluble carriers are aminoalkyl-Sepharoses, e.g. aminopropyl or aminohexyl Sepharose, and aminopropyl-glass. Other carriers may also be used which are modified to contain a chemically linked amino group. Such carriers may be derived from polysaccharides to which an aminoalkyl group is attached through a covalent linkage.

According to one aspect of the present invention, the O-acetyl groups on positions 7 and/or 8 of the sialyl moieties in the group C polysaccharide from OAc+ strains are selectively removed to a varying extent from the meningococcal group C polysaccharide by treatment with an appropriate reagent. Many deacetylating reagents are known to those skilled in the art. Preferably, the deacetylation is carried out under mild basic conditions in aqueous medium, such as, in about 0.01 to 0.5N sodium hydroxide, preferably 0.1N sodium hydroxide at about 0 to 50° C., preferably 25° C. Other basic solutions, such as potassium hydroxide, ammonium hydroxide and the like, can also be used for this reaction. The deacetylation reaction temperature and base concentration used in the reaction can be varied keeping in mind only that mild condition should be maintained. It is preferred that the reaction conditions should be controlled such that only deacetylation of the group C polysaccharide is achieved to the desired extent. The O-deacetylation is carried out until the desired degree of deacetylation is achieved , i.e., for about 1 to 25 hours, preferably for about 16 hours in 0.1N NaOH.

The yield of the O-deacetylated polysaccharide from the deacetylation reaction using mild conditions is typically in excess of 80%. The degree of O-deacetylation may vary from about 30% to 100% depending on the conditions employed. Typically, varying the temperature and reaction time allows one to vary the degree of O-deacetylation on the polysaccharide. It is preferred that O-deacetylation in the range of greater than 80% and most preferably 100% deacetylation is achieved.

It may also be desirable to fragment or depolymerize the polysaccharide chain prior to conjugation to the carrier molecule. Polysaccharides are sensitive to many reagents and may be hydrolyzed with weak acids such as acetic acid or oxidized by reagents such as metaperiodate. In a preferred embodiment of the present invention, deacetylated polysaccharide or polysacchardie from OAc− strains is both fragmented and activated for conjugation by metaperiodate oxidation. Those skilled in the art would recognize other methods for accomplishing this step of the reaction.

The immunogenic conjugates of the invention are prepared by first forming reducing end groups on fragments of the O-deacetylated GCMP or the polysaccharide from OAc− strains and then reacting the reducing end groups with amine groups of the carrier material or molecule by means of reductive amination. The reducing end groups may be formed by any suitable method, including selective hydrolysis, i.e., by acids or enzymes, or by oxidative cleavage, i.e., by metaperiodate. The conjugation is preferably achieved by reductive amination in an aqueous solution containing a reducing agent such as cyanoborohydride anions. Other methods for coupling a polysaccharide to a carrier molecule are known to one skilled in the art.

A preferred method for coupling involves a two step reaction. The polysaccharide is metaperiodate oxidized to create aldehyde moieties and is then reacted in the presence of free amino groups on the carrier molecule and in the presence of a suitable reducing agent. Suitable reducing agents would typically include cyanoborohydride, sodium borohydride or another reducing agent which will not reduce the reducing ends of interest nor adversely affect the carrier molecule or material. The reducing agent acts as a mild selective reducing agent of the Schiff base intermediate formed between the carbonyl groups of the hydrolyzed GCMP fragment and the amino groups of the carrier molecule or material. Typical reaction conditions for this type of conjugation are given in the Jennings et al. U.S. Pat. No. 4,356,170, which has been incorporated in toto by reference.

It is to be understood, however, that the conjugate vaccines of the invention are not limited to those produced via reductive amination. Thus, the vaccines may also be produced by conjugating the polysaccharide with the carrier protein using an adipic dihydrazide spacer, as described by Schneerson, R., et al, Preparation, Characterization and Immunogenicity of Haemophilus Influenzae Type b Polysaccharide-Protein Conjugates, *J. Exp. Med.,* 1952, 361–476 (1980), and in U.S. Pat. No. 4,644,059 to Lance K. Gordon. Alternatively, there may be used the binary spacer technology as described by Marburg, S., et al, "Biomolecular Chemistry of Macromolecules: Synthesis of Bacterial Polysaccharide Conjugates with *Neisseria meningitidus* Membrane Protein", *J. Am. Chem. Soc.,* 108, 5282–5287 (1986) or, possibly, the reducing ends methodology, as referred to by Anderson in U.S. Pat. No. 4,673,574. The disclosures of these citations are incorporated herein in toto by reference thereto.

The immunogenic conjugates of the invention may be formulated with one or more pharmaceutically acceptable excepients and optionally other ingredients. The pharmaceutically acceptable excipient(s) must be "acceptable" in the sense of being compatible with the other ingredients of the formulation and not deleterious to the recipient thereof. The formulations may conveniently be presented in unit dosage form and may be prepared by any method well-known in the pharmaceutical art.

Preparation of vaccines which contain polysaccharide conjugates as active ingredients is well understood in the art. Typically, such vaccines are prepared as injectables either as liquid solutions or suspensions; solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccine. Any suitable adjuvant known to those skilled in the art may be used. Suitable adjuvants include inter alia, aluminum hydroxide, aluminum phosphate and aluminum sulfate. The vaccines are conventionally administered parenterally, by injection, for example, either subcutaneously or intramuscularly. Additional formulations which are suitable for other modes of administration include suppositories and, in some case, oral formulations. For suppositories, traditional binders and carriers may include, for example, polyalkalene glycols or triglycerides; such suppositories may be formed from mixtures containing the active ingredient in the range of 0.5% to 10%, preferably 1-2%. Oral formulations include such normally employed excipients as, for example, pharmaceutical grades of mannitol, cellulose, magnesium carbonate and the like. These compositions take the form of solutions, suspensions, tablets, pills, capsules, sustained release formulations or powders and contain 10%-95% of active ingredient, preferably 25-70%.

The vaccines are administered in a manner compatible with dosage formulation, and in such amount as will be therapeutically effective and immunogenic. The quantity to be administered depends on the subject to be treated, capacity of the subject's immune system to synthesize antibodies, and the degree of protection desired. Precise amounts of active ingredient required to be administered depend on the judgment of the practitioner and are peculiar to each individual. However, suitable dosage ranges are of the order of several hundred micrograms active ingredient per individual. Suitable regimes for initial administration and booster shots are also variable, but are typified by an initial administration followed in one or two week intervals by a subsequent injection or other administration.

The vaccine of the present invention elicits effective levels of anti-GCMP antibodies in mammals. This vaccine may be administered by injection to mammals of any age and may be utilized to induce active immunization against systemic infection caused by *Neisseria meningitidis* by administering an immunogenic amount of the conjugate mammals susceptible to the disease.

Generally, vaccines containing from about 5 to about 100 μg, preferably about 10 to 50 μg, are suitable to elicit effective levels of antibody against GCMP in young mammals. The exact dosage would be determined by experimentation. Several small doses given sequentially would be expected to be superior to the same amount of conjugate given as a single injection.

In yet another aspect, the invention provides a gamma globulin fraction capable of protection against meningitidis caused by group C *N meningitidis*. The fraction is produced by immunizing a mammal with the vaccine of the present invention. The fraction is then administered to an individual to provide protection against or to treat on-going infection caused by the above organisms. From this, it will be appreciated that the immunogenic vaccine conjugates of the invention will provide for a source of therapeutic antiserum in light of their favorable immunogenicity. The conjugates of the invention will also be useful for raising monoclonal antibodies and, possibly, anti-idiotype antibodies.

O-Deacetylation of the meningococcal group C polysaccharide can be carried out by treatment with mild base such as, 0.01 to 0.5N NaOH preferably 0.1N NaOH at about 0° to 50° C., preferably 25° C. for about 1 to 25 hours, preferably about 16 hours. The removal of the acetyl groups from the 7 and/or 8 positions is verified by NMR spectroscopy.

In the subsequent steps the polysaccharide is purified by gel filtration such as, on Superdex 200 prep grade. Preferably, reductive partial depolymerization using sodium periodate is carried out on both the deacetylated polysacchardie form OAc+ strains and the polysacchardie from OAc− strains to afford an activated polysaccharide having the optimal size for eliciting the maximal immune response. The polysaccharide is purified by gel filtration, dialyzed to remove salts and lyophilized. It is then coupled to an appropriate protein carrier such as tetanus toxoid by the reductive amination reaction. The resulting conjugates are purified by gel filtration and analyzed for immunogenicity in FRW outbred Swiss Webster mice purchased from Charles Rivers.

EXAMPLE 1

O-Deacetylation of Group C Meningococcal Polysaccharide (GCMP)

Native meningococcal group C polysaccharide (188 mg) was dissolved in 0.1 N sodium hydroxide solution (30 ml). The mixture was stirred at 25° C. for 16 hrs. It was then dialyzed at 4° C. against water and lyophilized. The polysaccharide (144 mg, 77%) which was obtained as a white cottony solid was shown by $^1$H-N.M.R. spectroscopy (500 MHz) to be O-deacetylated.

EXAMPLE 2

Purification of the O-Deacetylated Group C Polysaccharide (GCMP)-(−)

The O-deacetylated polysaccharide (141 mg) was dissolved in Dulbecco's PBS (10 mL) and purified by gel filtration on a Superdex 200 prep grade (2.6×100 cm) column. The column was eluted at 100 ml/hr and 5.0 ml fractions were collected. The eluate was monitored with a differential refractometer and a UV (280 nm) detector. The fractions containing the first major peak detected with the differential refractometer and which were substantially free of UV absorbing material were combined. After dialysis against water and lyophilization purified GCMP-(−) (108 mg, 77%) was obtained as a white cottony solid. The solid material was analyzed for protein by the Bradford method and for nucleic acids by the UV absorbance at 260 nm. As shown in Table 1 these contaminants are substantially reduced by this purification step. In addition analysis of GCMP-(−) by HPLC using the Superose 12 gel filtration column (Pharmacia) showed that it elutes as a sharp void volume peak as it was also observed for the starting native polysaccharide (GCMP) indicating that the purified polysaccharide is present in a high molecular weight form.

EXAMPLE 3

Oxidation and Sizing of Purified GCMP-(−)

The oxidation of the polysaccharide with sodium metaperiodate serves the dual purpose of activating the polysaccharide for subsequent coupling to proteins and to cleave the polysaccharide into smaller fragments which have been shown previously to give the optimal immune response. Since it has been also shown previously that different lots of polysaccharide require different periodate oxidation conditions in order to achieve the optimal polysaccharide chain lengths these conditions are first determined on small scale reactions (5 mg) after which the large scale reaction is performed. Typically the reaction time and temperature is kept constant at 2 hours and 25° C. respectively and the concentration of the sodium metaperiodate is varied between 3 and 12 millimolar in deionized water. The concentration of the polysaccharide in the small and large scale reactions is also kept constant at 6–10 mg/ml. At the end of the 2 hour period at an excess (~10-fold) of a 1.0M ethylene glycol solution is added to the reaction solution in order to destroy unreacted sodium metaperiodate. Following at least 30 minutes of reaction the solutions are analyzed by FPLC using a calibrated Superose-12 column in order to determine the average molecular weight of the oxidized polysaccharide. The reaction conditions which provide the polysaccharide having an average molecular weight of 12,000–16,000 daltons are used in the large scale reactions as illustrated by the following reaction.

Purified GCMP-(−) (63 mg) was dissolved in deionized water (4.81 ml). To this solution was added a 21 mmol sodium metaperiodate solution (4.81 mL) to give a reaction mixture in deionized water having the polysaccharide at 6.55 mg/mL and the NaIO$_4$ at 10.5 mmol. The reaction was allowed to proceed at 25° C. for 2 hours in the dark and then treated with 1 M ethylene glycol (0.96 Ml) for 30 min. This material elutes on the Superose-12 column as a broad peak having an average molecular weight of 12,800 daltons. The volume of the solution was reduced to about 5 Ml on the lyophilizer and the material was purified by gel filtration on a Superdex 200 prep grade column (2.6×100 cm) using Dulbecco's PBS as the eluting buffer and 5 mL fractions were collected. Those fractions which contained material having an average molecular weight between 10,000–18,000 were combined. After dialysis against deionized water and lyophilization the oxidized and sized polysaccharide [o]-GCMP-(−) (16.0 mg, 23%) was obtained as a white cottony solid which was shown by FPLC on Superose-12 to have an average molecular weight of 14,500 daltons.

TABLE 1

Protein and nucleic acid contents of group C Meningococcal polysaccharide preparations

| Polysaccharide | % Protein | % Nucleic Acids |
|---|---|---|
| GCMP | 8.3 | 2.7 |
| Purified GCMP-(−) | 0.61 | 0.12 |
| [o]-GCMP-(−) | 0.06 | 0.31 |

EXAMPLE 4

Preparation of [o]-GCMP-(+)

Native GCMP (350 mg) was dissolved in 0.02N NaOH (36 mL) and incubated at 25° C. for 3 hours. To this solution was then added 0.1M NaIO$_4$ (36 mL) and the contents were incubated at 25° C. a further 50 min. The reaction was then treated with 50% ethylene glycol (5.3 mL) for 20 min. and the mixture was clarified by centrifugation at 5000 rpm for 10 min. The supernatant was dialyzed against deionized water and lyophilized to afford 300 mg of solid. The material was sized on Bio-Gel A-0.5 m column to provide the oxidized and sized polysaccharide {[o]-GCMP-(+)} having a molecular weight of 11,500 daltons.

EXAMPLE 5

Purification of the Tetanus Toxoid Protein Monomer (TT)

Into a gently stirred tetanus toxoid solution (Statens Seruminstitu) [containing 2.1 mg/mL of protein (Bradford protein assay using human IgG as standard)] (75 mL) was added in small portions over a period of 45 min ammonium sulfate (42.1 g) to give an 80% saturated solution. The turbid solution was left at 4° C. overnight to complete the precipitation of the protein. The precipitate was collected by centrifugation at 15,000 rpm (23,000 g) for 20 min and the supernatant which contained less than 10% of the original protein was discarded. The pellet was redissolved in Dulbecco's PBS buffer (10 mL) and fractionated by gel filtration on a Bio-Gel A-0.5 m column. The major peak corresponding to the tetanus toxoid monomer was pooled dialyzed against deionized water and lyophilized to give TT as a white cottony solid (65.4 mg, 41%).

EXAMPLE 6

Coupling of O-deacetylated Group C Meningococcal Polysaccharide {[o]-GCMP-(−)} to Tetanus Toxoid (TT)

A solution containing [o]-GCMP-(−) (10 mg), TT (3.3 mg) and sodium cyanoborohydride (6.8 mg) in 0.20M phosphate buffer pH 7.5 (0,222 mL) was kept at 37° C. for 4 days. The reaction solution was diluted with PBS buffer (0.5 mL) and insoluble matter was removed by centrifugation in an Eppendorf centrifuge at 10,000 rpm for 2 min. The supernatant was loaded unto a 1.6×100 cm Bio-Gel A-0.5 m column and eluted with 0.15M NaCl+0.02% thimerosal at 20 mL/hr. Fractions corresponding to the peak eluting at the void volume were pooled to afford the O-deacetylated group C meningococcal polysaccharide-tetanus toxoid conjugate [GCMP-(−)TT]. The pooled solution was analyzed for protein by the Bradford method and shown to contain 2.86 mg of protein (87% yield). The polysaccharide content in the conjugate was estimated from the content of sialic acid, which was determined by the resorcinol assay for sialic acid, and was shown to contain 0.997 mg of polysaccharide (10% yield). The characteristics of the conjugate are summarized in Table 2.

EXAMPLE 7

Coupling of O-Acetylated Group C Meningococcal Polysaccharide {[o]-GCMP-(+)} to Tetanus Toxoid A solution containing [o]-GCMP-(+) (10.2 mg), TT (2.9 mg) and sodium cyanoborohydride (5.2 mg) in 0.20M phosphate buffer pH 7.5 (0.20 mL) was kept at 37° C. for 5 days. The conjugate was purified y gel filtration chromatography and analyzed as described in Example 6. This conjugate solution contains 2.7 mg (93% yield) of protein and 1.06 mg (10.4% yield) of polysaccharide. The characteristics of this conjugate are summarized in Table 2.

TABLE 2

Characteristics of the GCMP-(−)-TT and GCMP-(+)-TT conjugates

| Conjugate | Polysaccharide | | Protein:PS Ratio | % Polysaccharide in the Conjugate |
|---|---|---|---|---|
| | Acetylation | Average mol. Wt. | | |
| GCMP-(−)-TT | O-Deacetylated | 12,500 | 2.9:1 | 26 |
| GCMP-(+)-TT | O-Acetylated | 11,500 | 2.6:1 | 28 |

EXAMPLE 7A

Preparation of (−)-GCMP-TT Vaccine

The (−)-GCMP-TT vaccines are prepared in the same manner as the GCMP-(−)-TT vaccines in the above examples except that the polysaccharide is obtained from N. meningitidis group C strain MC bacteria. This bacteria produces GCMP which lacks the O-acetyl moieties.

EXAMPLE 8

Preparation of the Conjugate Vaccine Solutions and Biological Studies

The conjugate solutions described in Examples 6 and 7 were diluted with saline (0.15M NaCl+0.02% thimerosal) such that the concentration of polysaccharide in all of the vaccines is 10 μg/mL. Half of these vaccines also contained the aluminum hydroxide adjuvant at a concentration of 1.0 mg/mL.

The immunogenicities of these vaccines were assayed in 4–6 week old outbred Swiss Webster CFW female mice. The animals were injected subcutaneously with 0.2 mL of the vaccines on day 0, 14 and 28 and the sera for antibody assay were collected on day 38.

EXAMPLE 9

Enzyme-Linked Immunosorbant Assay (ELISA) for Mouse Antibodies to Neisseria meningitidis Group C Polysaccharide The ELISA was performed by coating microtiter plates with the appropriate polysaccharide [GCMP-(−) or GCMP-(+)] human serum albumin (HSA) conjugate followed by treatment with BSA blocking buffer. Dilutions of the sera in PBS-Tween buffer were then applied. The plates were incubated at room temperature for 1 hour, washed and treated with the second antibody [goat antimouse IgG (H+L) - peroxidase] at room temperature for 30 minutes. This was followed by thorough washing with PBS-Tween and treatment with freshly prepared TMB peroxidase substrate, as described in Kirkegaard & Perry (please insert citation). After 15 minutes, the enzyme reaction was stopped with 1M phosphoric acid added to each well, and the absorbance was analyzed using a microplate reader. The ELISA titers are summarized in Table 3.

EXAMPLE 10

Bactericidal Assay for Neisseria Meningitidis Serogroup C

The bactericidal activity was assayed by incubating Neisseria meningitidis group C (strain C11) in the presence of an appropriate dilution of the test sera and baby rabbit serum (complement source) at 37° C. for 1 hr. Two negative controls, in one case lacking the test sera and in the second case containing heat inactivated complement were similarly incubated. Aliquots of these solutions (50 μl) were then applied unto chocolate agar plates in duplicate and incubated at 35°–37° C. in 5% $CO_2$ overnight in order to assay for survivors. The next morning the number of colonies are counted on each plate and averages calculated for the duplicates. The serum bactericidal titer is reported as the serum dilution yielding 50% survival. The bactericidal activities for the different vaccines are summarized in Table 3

TABLE 3

| Vaccine | | ELISA titer | Bactericidal titer |
|---|---|---|---|
| GCMP-(+) | in Saline | 230 | No Response |
| GCMP-(+)-TT | in Saline | 12,293 | No Response |
| GCKP-(+)-TT | in Saline and Alum | 27,866 | 2,800 |
| GCMP-(−)-TT | in Saline | 13,127 | 2,700 |
| GCMP-(−)-TT | in Saline and Alum | 25,537 | 21,000 |
| (−)-GCMP-TT[1] | Saline | 10,867 | 2,700 |
| (−)-GCMP-TT[1] | Alum | 27,327 | >40K |

Analysis of the sera obtained from groups of mice immunized with the two types of conjugate by ELISA revealed the presence of high titers of IgG antibody in both groups of mice. Further analysis of the sera using a bactericidal assay against the modified strain revealed a surprising result. While the ELISA titer for sera obtained from both vaccine groups were similar, the sera obtained from mice immunized with the modified conjugate had superior levels of bactericidal antibodies when compared to sera from mice that had received the native conjugate vaccine. The results of this study suggest that the present conjugate vaccine elicit a class of antibodies that have potent bactericidal activity.

It is understood that the examples and embodiments described herein are for illustrative purposes only and that various modifications or changes in light thereof will suggest to persons skilled in the art to be included within the spirit and purview of this application and scope of the appended claims.

We claim:

1. A method of immunizing mammals against N. menigitidis infection, said method comprising the step of administering to the mammals subject to said infection a therapeutically effective amount of a vaccine comprising a pharmaceutically acceptable injectable excipient and an immunogenic conjugate comprising a suitable carrier covalently coupled to an O-deacetylated group C meningococcal polysaccharide or fragment thereof, wherein the degree of deacetylation is at least 80%.

2. A method of immunizing mammals against N. menigitidis infection,s aid method comprising the step of administering to the mammals subject to said infection a therapeutically effective amount of a vaccine comprising a pharmaceutically acceptable injectable excipient and an antigenic conjugate to an O-deacetylated polysaccharide of group C Neisseria meningitidis or a fragment thereof, in which the degree of O-deacetylation is greater than about 80%.

3. A method according to claim 1 or 2, comprising parenterally administering said vaccine.

4. A method according to claim 1 or 2, wherein the vaccine is administered in an dosage amount of about 1 to 25 microgram per kilogram body weight.

5. A method of preparing an immunogenic conjugate comprising the steps of:
   i) O-deacetylating a meningococcal group c polysaccharide or a fragment thereof under conditions which remove at least 80% of the O-acetyl groups;
   ii) activating the deacetylated polysaccharide for coupling; and,
   iii) coupling the deacetylated polysaccharide with a carrier molecule.

6. The method according to claim 5 further comprising generating meningococcal group C polysaccharide fragments by depolymerization of the polysaccharide using sodium periodate.

7. The method according to claim 5 wherein said activating of the polysaccharide is carried out with sodium metaperiodate.

8. The method according to claim 5, wherein the coupling is carried out by reductive amination.

9. The method according to claim 8, wherein reductive amination is carried out in the presence of cyanoborohydride.

* * * * *

UNITED STATES PATENT AND TRADEMARK OFFICE
CERTIFICATE OF CORRECTION

PATENT NO. : 5,425,946
DATED : June 20, 1995
INVENTOR(S) : Joseph Y. Tai, Lucjan J.J. Hronowski, and Sharon Mates It is certified that error appears in the above-identified patent and that said Letters Patent is hereby corrected as shown below:

Title page,
The named inventors should read -- Francis Michon, Bethesda, MD; Harold Jennings, Gloucester, Ontario; Joseph Tai, Collegeville, PA; Lucjan Hronowski, Bedford, MA; and Sharon Mates, Chevy Chase, MD --.

Signed and Sealed this

Thirtieth Day of October, 2001

Attest:

NICHOLAS P. GODICI
Attesting Officer    Acting Director of the United States Patent and Trademark Office